(12) United States Patent
Huddleston

(10) Patent No.: US 11,808,237 B2
(45) Date of Patent: Nov. 7, 2023

(54) THERMAL CRACKER FOR COMBUSTIBLE AND FLAMMABLE LIQUIDS FOR ENGINES

(71) Applicant: Sky Moon Huddleston, Bourbon, MO (US)

(72) Inventor: Sky Moon Huddleston, Bourbon, MO (US)

( * ) Notice: Subject to any disclaimer, the term of this patent is extended or adjusted under 35 U.S.C. 154(b) by 0 days.

(21) Appl. No.: 17/368,702

(22) Filed: Jul. 6, 2021

(65) Prior Publication Data
US 2022/0003190 A1 Jan. 6, 2022

Related U.S. Application Data

(60) Provisional application No. 63/048,322, filed on Jul. 6, 2020.

(51) Int. Cl.
| | |
|---|---|
| F02M 21/02 | (2006.01) |
| F02M 31/125 | (2006.01) |
| F02M 27/02 | (2006.01) |
| F02B 43/04 | (2006.01) |
| C10L 3/00 | (2006.01) |
| C10L 3/12 | (2006.01) |

(Continued)

(52) U.S. Cl.
CPC ............ *F02M 21/0227* (2013.01); *B01J 6/00* (2013.01); *C07C 4/04* (2013.01); *C10L 3/00* (2013.01); *C10L 3/12* (2013.01); *F02B 43/04* (2013.01); *F02M 21/0209* (2013.01); *F02M 21/0242* (2013.01); *F02M 27/02* (2013.01); *F02M 31/125* (2013.01); *C10L 2290/02* (2013.01)

(58) Field of Classification Search
CPC ........... F02M 21/0227; F02M 21/0209; F02M 21/0242; F02M 27/02; F02M 31/125; B01J 6/00; B01J 3/008; C07C 4/04; C10L 3/00; C10L 3/12; C10L 2290/02; C10L 2290/06; C10L 2290/28; C10L 2290/46; F02B 43/04; Y02P 20/54; Y02T 10/12; Y02T 10/30

See application file for complete search history.

(56) References Cited

U.S. PATENT DOCUMENTS

| | | | |
|---|---|---|---|
| 1,970,010 A | * 8/1934 | Long | F02M 1/00 |
| | | | 123/557 |
| 2018/0274481 A1 | * 9/2018 | Silva | F02M 31/02 |

FOREIGN PATENT DOCUMENTS

KR 20040072990 A * 8/2004

* cited by examiner

*Primary Examiner* — Grant Moubry
*Assistant Examiner* — Charles J Brauch

(57) ABSTRACT

The present invention relates to a combination of components suitable to break down liquid fuels into short chain molecules and gaseous states of matter by heating and pressurizing the combustible/flammable liquids to the point where they phase change into a supercritical fluid, then releasing some fluid as needed into a vapor accumulation tank that has a lower pressure. This subsequent drop in pressure phase changes the fluid from a supercritical state into a consistent and safe gaseous state. From there, the fuel can be delivered to the engine via direct injectors, gaseous fuel carburetors, or a regulating valve such as a needle valve. Because gaseous fuels readily homogenize with intake air and oxidizers, the present invention allows any engine to cleanly, reliably, and consistent use any fuel without adjustment. This allows any engine to run off any combustible liquid, in effect creating the ultimate multifuel system.

19 Claims, 1 Drawing Sheet

(51) Int. Cl.
*C07C 4/04* (2006.01)
*B01J 6/00* (2006.01)

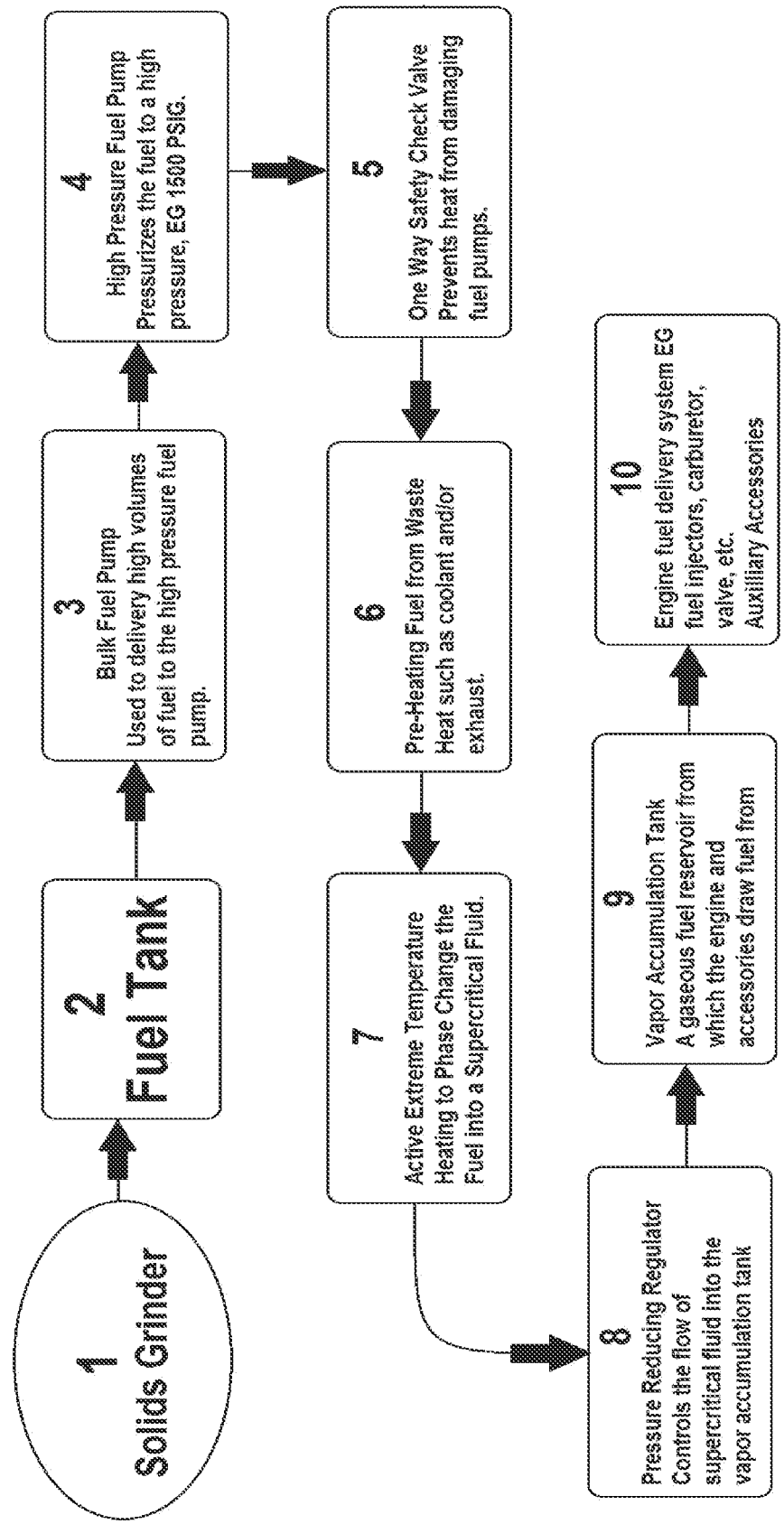

THERMAL CRACKER FOR COMBUSTIBLE AND FLAMMABLE LIQUIDS FOR ENGINES

Priority is claimed to 63/048,322 filed on Jul. 6, 2020.

BACKGROUND OF INVENTION

Most engines and fuel systems currently in production are designed for one specific fuel type/source. This greatly limits fuel flexibility and has been a major hindrance to the viability of alternative, renewable, and green fuels. Furthermore, long chained liquid fuels reduce the efficiency of engine systems because the heat from the combustion of the fuel is required to overcome the latent heat loss to evaporate and chemically break down the fuel before oxygen from the intake charge can bond with the hydrogen, oxygen, and various other combustible elements found in liquid fuels.

When using liquid fuels, including direct injected liquids, no matter how well atomized the fuel is the liquid droplets are still a stratified charge that will sap heat from the engine via latent heat loss via evaporation and chemical breakdown before oxidation/combustion of the fuel can occur. This inherently means that all liquid fuel systems use a stratified charge, and can never become a true homogeneous charge. Because liquid state fuels in a stratified charge carry sound, shock, and impact waves more readily, this makes stratified charges far more susceptible to detonation and "engine knock" conditions when higher compression ratio's are used. This has been one of the primary limiting factors for engine efficiency since the beginning of the internal combustion engine.

Gaseous fuels such as methane and propane have exceptionally higher octane ratings in both RON and MON. This is partially due to the fact that gaseous fuels readily and naturally homogenize with intake air and partially because of their shorter and simpler molecular structure. These true homogeneous charges allow engines using gaseous fuels to run much higher compression ratio's, which greatly increases the efficiency, power to weight ratio, and performance of the engine. Gaseous fuels such as propane and methane also have higher energy density's by weight because the fuel does not need to waste its own energy to break itself down to continue the propagation of the flamefront. This is why methane has the highest energy density by weight of any common hydrocarbon as it is one of the shortest and simplest hydrocarbons. By observing the various types and lengths of hydrocarbons we recognize a general pattern, that the shorter and simpler a hydrocarbon is, on average, the higher its octane rating and energy density by weight will be. In effect, the shorter and simpler the hydrocarbon is, the more energy per atom of hydrogen and carbon burned can be extracted.

However, gaseous fuels such as methane have lower the energy density by volume. Gaseous fuels also require complex pressurized fuel storage and transportation method, and can be dangerous if these storage systems are structurally compromised as the fuel will naturally homogenize with atmospheric air and become susceptible to exploding. Furthermore, these fuels are seldom readily available on demand and infrastructure for their distribution and usage is lacking, whereas liquid fuel infrastructure is abundant and readily available.

OBJECTIVES OF THE INVENTION

Thus it is the objective of the present invention to combine the best attributes of liquid fuel systems with that of gaseous fuel systems. This allows the present invention to achieve capabilities whose sum is greater than the whole of either gaseous or liquid fuel systems, as the present invention can allow any engine to readily use any combustible liquid. In addition to readily available fuels such as gasoline, diesel, and jet fuel, even combustible liquids currently not even considered as acceptable fuels can be used, including but not limited to untreated/unrefined waste vegetable oils, waste motor/lubrication oil, crude oil, used brake fluid, coal/charcoal water slurry's, bunker oil, depolymerized plastics and biomatter, waste ketones, and waste solvents such as used paint thinners/strippers, lacquers, varnishes, etc. Furthermore, by breaking down these combustible liquids into shorter chained and simpler molecular structures that are gaseous, this allows an engine to operate with a true homogeneous charge which allows engines to run higher compression ratio's and thus increased efficiency. This also allows the engine to operate with any fuel without adjustment, as the present invention actively converts liquid fuels into consistent gaseous fuels. Thus to the engines perspective, it is only ever receiving a consistent gaseous homogeneous charge of fuel and air/oxidizer. The present invention also increases engine and system efficiency by using waste heat, other heat sources, and catalysts to break down and phase change the fuel into a gaseous state rather than primary heat sources such as the inside of the combustion chamber/cylinder as most engines in use currently do. Additionally, for applications when the present invention is coupled to pulse detonation engines, a throttle plate to control airflow can be eliminated and engine torque and RPM can instead be controlled by actively varying fuel (energy) input into the engines intake plenum by opening/closing a valve more or less as energy is required. This allows an engine to operate at its maximum volumetric efficiency throughout its entire RPM band and thus the rate of fuel consumption is now determined exclusively by the load. This allows for the immense simplification of the fuel delivery system, as instead of a complex carburetor or fuel injection system, a simple valve such as a needle valve may be used to control and regulate fuel delivery.

SUMMARY OF PRESENT INVENTION

The present invention is an on demand fuel processing system that converts any combustible liquid into a consistent gaseous fuel. This is achieved by first pressurizing the fuel using a high pressure fuel pump. The pressurized fuel goes through a one way safety check valve, and then enters a section of tubing or a chamber where the fuel is heated via waste heat from the engine and active heat sources such as induction coils, resistant heaters, and/or hydrosonic bubble cavitation pumps/heaters. This phase changes the fuel into a different state of matter called a supercritical fluid where it obtains some of the property's of a gas whilst retaining some of the properties of a liquid. Catalysts packed inside the supercritical fluid tank to promote faster, less energy intensive, and more efficient breakdown of the fuel into simpler and smaller molecular structures. As fuel is drawn from the vapor accumulation tank, a pressure reducing regulator releases a portion of supercritical fluid into a vapor accumulation tank to refill it. Because the vapor accumulation tank is under considerably less pressure this causes a phase change to a gaseous state when the supercritical fluid enters the vapor accumulation tank. From the vapor accumulation tank, the fuel can be routed to fuel injectors such as those used for LPG and CNG, it can be routed to CNG/LPG carburetors, or can be routed to a valve to control engine power output by fuel input. Furthermore, the gaseous fuel from the vapor accumulation tank can be used to power other engines, generators, equipment, and accessory's such as grills, heaters, bunsen burners, torches, and various other devices as the gaseous state fuel produced by the present invention is similar to methane, propane, LPG, and other gaseous fuels.

BRIEF DESCRIPTION OF THE DRAWINGS

FIG. 1 exhibits a flowchart of the various components and parts of the present invention and the stages and phases by which the present invention operates and functions by.

DETAILED DESCRIPTION OF VARIOUS EMBODIMENT'S

There are several stages to the present invention. The first stage is an optional solids grinder (1). This grinder can be installed behind or in front of the filler neck of the fuel tank to grind solid fuel into fine dust suitable for chemical breakdown. Solids such as coal, charcoal, pulp, sawdust, feces, plastics, and various other waste matter can be ground and mixed with liquid fuels. The second stage is the fuel tank (2), where fuel is stored. The third stage is an optional bulk low pressure fuel pump (3) that delivers fuel to the fourth stage. The fourth stage is a high pressure fuel pump (4). It is recommended to pressurize the fuel to at least 1500 PSIG so that any combustible liquid may be used. This fourth stage increases fuel pressure to prepare the fuel to be phase changed during the sixth and seventh stage. The fifth stage is a one way check valve (5) for safety, to prevent thermal energy from the heated supercritical fluid from backing into the fuel pump (4). The sixth stage is an optional fuel preheater (6) that uses waste heat such as coolant, exhaust gases, or other heat sources to preheat the fuel and reduce the required load of the active fuel heater (7). The seventh stage is the supercritical fluid chamber (7), which heats the pressurized liquid to temperatures above that required to phase change the liquid fuel into a supercritical fluid. It is recommended to heat the liquid to 1000 F. so that any combustible liquid can be used. Pressures and temperatures lower than this may limit the fuel versatility of the system. Heating of the liquid can be achieved using active heating such as induction and resistance heating, and a fuel pump may also be used to heat the fluid if a hydrosonic bubble cavitation pump is used. A hydrosonic bubble cavitation pump can in some alternative embodiment's serve to both pressurize and heat the fuel into a supercritical fluid. The supercritical fluid line/tank (7) can be packed with catalysts to increase efficiency and fuel versatility. The 8$^{th}$ stage is a pressure reducing regulator (8). The pressure reducing regulator (8) can be actively controlled by electronic means, or can be passively controlled by using a mechanical pressure reducing regulator valve. The pressure reducing regulator (8) serves to consistently feed supercritical fluid into the ninth stage according to the load of the engine and demand of fuel consumption of the auxiliary accessory's. The ninth stage is the vapor accumulation tank (9). This tank ensures a consistent pressure is fed to the injectors, carburetor(s), or control valve(s), and also serves the same function for fuel consuming auxiliary accessory's. In this respect the vapor accumulation tank can be likened to how a capacitor is used in many electronic circuits. The vapor accumulation tank can also be packed with catalysts to further increase efficiency and break down the fuel. The 10$^{th}$ and final stage is delivery of gaseous fuel to the engines fuel delivery system (10), which can be a simple valve, fuel injectors, a gaseous fuel carburetor, etc. and auxiliary accessory's if applicable.

I claim:

1. A thermal cracker comprising:
a high pressure fuel pump;
a chamber configured to receive fuel from said high pressure fuel pump;
a heat source configured to heat said fuel to produce a supercritical fluid formed in said chamber; and
a vapor accumulation tank, to receive said supercritical fluid from said chamber via a pressure reducing regulator, the vapor accumulation tank configured to store said supercritical fluid therein in gaseous form at a consistent pressure for eventual delivery to a downstream component.

2. The thermal cracker of claim 1, further comprising a safety check valve.

3. The thermal cracker of claim 2, wherein said safety check valve is one way.

4. The thermal cracker of claim 1, wherein an engine draws gaseous fuel from said vapor accumulation tank.

5. The thermal cracker of claim 1, wherein said heat source is waste heat.

6. The thermal cracker of claim 1, further comprising at least one catalyst.

7. The thermal cracker of claim 1, wherein said chamber is a tube.

8. The thermal cracker of claim 1, wherein said downstream component is selected from the group consisting of an engine fuel delivery system, a generator, a grill, a heater, a Bunsen burner, and a torch.

9. The thermal cracker of claim 1, wherein said vapor accumulation tank contains at least one catalyst.

10. The thermal cracker of claim 1, wherein said pressure reducing regulator causes said supercritical fluid to convert to said gaseous form in said vapor accumulation tank.

11. The thermal cracker of claim 3, wherein said heat source is waste heat.

12. The thermal cracker of claim 3, further comprising at least one catalyst.

13. The thermal cracker of claim 4, wherein said heat source is waste heat.

14. The thermal cracker of claim 4, further comprising at least one catalyst.

15. The thermal cracker of claim 5, further comprising at least one catalyst.

16. The thermal cracker of claim 1, further comprising a fuel preheater.

17. The thermal cracker of claim 1, further comprising a hydrosonic bubble cavitation pump configured to pressurize and heat said fuel into said supercritical fluid.

18. The thermal cracker of claim 1, wherein said pressure reducing regulator is configured to consistently feed said supercritical fluid to said vapor accumulation tank.

19. The thermal cracker of claim 1, further comprising a safety check valve;
wherein said safety check valve is one way;
wherein said chamber is a tube;
wherein said heat source is waste heat;
further comprising at least one catalyst;
further comprising a fuel preheater;
further comprising a hydrosonic bubble cavitation pump configured to pressurize and heat said fuel into said supercritical fluid; and wherein said pressure reducing regulator is configured to consistently feed said supercritical fluid to said vapor accumulation tank.

\* \* \* \* \*